United States Patent [19]
Poorman

[11] Patent Number: 5,424,842
[45] Date of Patent: Jun. 13, 1995

[54] SELF-CLEANING SYSTEM FOR MONITORING THE OPACITY OF COMBUSTION ENGINE EXHAUST USING VENTURI EFFECT

[75] Inventor: Richard N. Poorman, Columbus, Ind.

[73] Assignee: Cummins Electronics Company, Inc., Columbus, Ind.

[21] Appl. No.: 307,276

[22] Filed: Sep. 16, 1994

Related U.S. Application Data

[63] Continuation of Ser. No. 53,491, Apr. 27, 1993, abandoned.

[51] Int. Cl.⁶ .............................................. G01N 21/00
[52] U.S. Cl. ...................................... 356/438; 356/439
[58] Field of Search ............... 356/437, 438, 439, 440; 359/509; 250/564, 573

[56] References Cited

U.S. PATENT DOCUMENTS

| | | |
|---|---|---|
| 3,814,004 | 6/1974 | Bignardi ............................ 356/438 |
| 3,954,342 | 5/1976 | Boeke . | |
| 4,066,364 | 1/1978 | Emerson ............................ 356/439 |
| 4,126,396 | 11/1978 | Hartmann et al. . | |
| 4,583,859 | 4/1986 | Hall, II . | |
| 4,647,780 | 3/1987 | Dunkel . | |

FOREIGN PATENT DOCUMENTS

| | | | |
|---|---|---|---|
| 0187846 | 9/1985 | Japan ................................... 356/438 |
| 1635084 | 3/1991 | Russian Federation ............ 356/348 |

Primary Examiner—Richard A. Rosenberger
Assistant Examiner—Robert Kim
Attorney, Agent, or Firm—James M. Durlacher; Woodard, Emhardt, Naughton, Moriarty & McNett

[57] ABSTRACT

A self-cleaning smoke-monitoring system that is used in measuring opacity of exhaust from an internal combustion engine. The invention includes a pair of air passages that supply a flow of filtered air over the optic elements of the smoke-monitoring system. The flow of particulate-free air is the result of a venturi effect created in the exhaust flow such that ambient air is continuously drawn in through the air ducts.

10 Claims, 1 Drawing Sheet

SELF-CLEANING SYSTEM FOR MONITORING THE OPACITY OF COMBUSTION ENGINE EXHAUST USING VENTURI EFFECT

This application is a continuation of application Ser. No. 08/053,491, filed Apr. 27, 1993, now abandoned.

BACKGROUND OF THE INVENTION

The present invention relates generally to a smoke-monitoring system for use in measuring the opacity of exhaust from an internal combustion engine, and in particular, to an unpowered system that maintains the exposed optical portions of the opacity monitor free of particulate contaminants.

In analyzing the performance of an internal combustion engine, it is often desirable and sometimes essential that the smoke content of the exhaust from the engine be measured and analyzed. This task is usually accomplished by using an opacity monitor that includes a light source and sensor mounted on opposite sides of the engine's exhaust pipe such that an optical path extends between the light source and the sensor across the exhaust stream. In order to protect the sensitive optics and electronics of the light source and sensor, these two portions of the opacity monitor are normally maintained in separate sealed compartments mounted on either side of the exhaust pipe of the engine. Each compartment includes a transparent window at one end such that the optical path extending between the light source and the sensor passes through the two windows. While the windows serve to protect the sensitive optical and electronic elements of the monitoring system, the transparency of the windows must be maintained in order to preserve the accuracy of the monitoring system. In other words, some means must be provided that prevents the build-up of particulate matter on the exposed faces of the windows.

In order to overcome this problem, many opacity monitors include a blower system that continuously blows particulate-free air across the exposed surface of the windows in order to prevent the exhaust smoke and other potential contaminants from coming into contact with the windows. This is accomplished by mounting the windows within air ducts that have inlets that open outside of the exhaust pipe and outlets which open into the exhaust pipe. Blowers mounted in the air ducts draw fresh air into the ducts through filters to continuously provide particulate-free air flow across the exposed faces of the windows. While the blower-type system may be acceptable in some applications, what is needed is an unpowered self-cleaning system that automatically maintains the cleanliness of the windows without requiring powered blowers or access to a compressed air supply.

SUMMARY OF THE INVENTION

A self-cleaning smoke-monitoring system that is used in measuring the opacity of exhaust from an internal combustion engine. The system includes an exhaust pipe attached to the engine for conveying exhaust from the engine. The system also includes a light source and sensor combination that is mounted adjacent the exhaust pipe in such a way that an optical path between the source and the sensor traverses the exhaust pipe. A first air duct mounted to the exhaust pipe has an outlet that opens into the exhaust pipe. A portion of the first air duct coincides with a portion of the optical path. A first window is attached to the first air duct between the inlet and the outlet and is positioned in the optical path. The light source is positioned outside the first air duct and adjacent the first window. A second air duct mounted to the exhaust pipe also includes an outlet that opens into the exhaust pipe. Also like the first air duct, a portion of the second duct coincides with a portion of the optical path. A second window is positioned in the optical path and attached to the second air duct between its inlet and outlet. The sensor is positioned outside the second air duct adjacent the second window. Inlet means is attached to both first and second air ducts for supplying ambient air to the air ducts. Filter means is attached to the air ducts for removing particulate matter from the ambient air entering the air ducts through said inlet means. A portion of the exhaust pipe, and a portion of the first and second air ducts adjacent their outlets are sized and arranged to create a venturi effect when the engine is running such that the fluid pressure of the exhaust from the engine adjacent the outlets is lower that the air pressure at the inlets of the air ducts. This causes air to be pulled through the air ducts and into the exhaust pipe when the engine is running; the result being that particulate-free air continuously passes over the exposed faces of the first and second windows.

One object of the present invention is to provide a self-cleaning smoke-monitoring system.

Another object of the present invention is to provide an improved smoke-monitoring system.

Related objects and advantages of the present invention will be apparent from the following description.

DESCRIPTION OF THE PREFERRED EMBODIMENT

Figure 1:
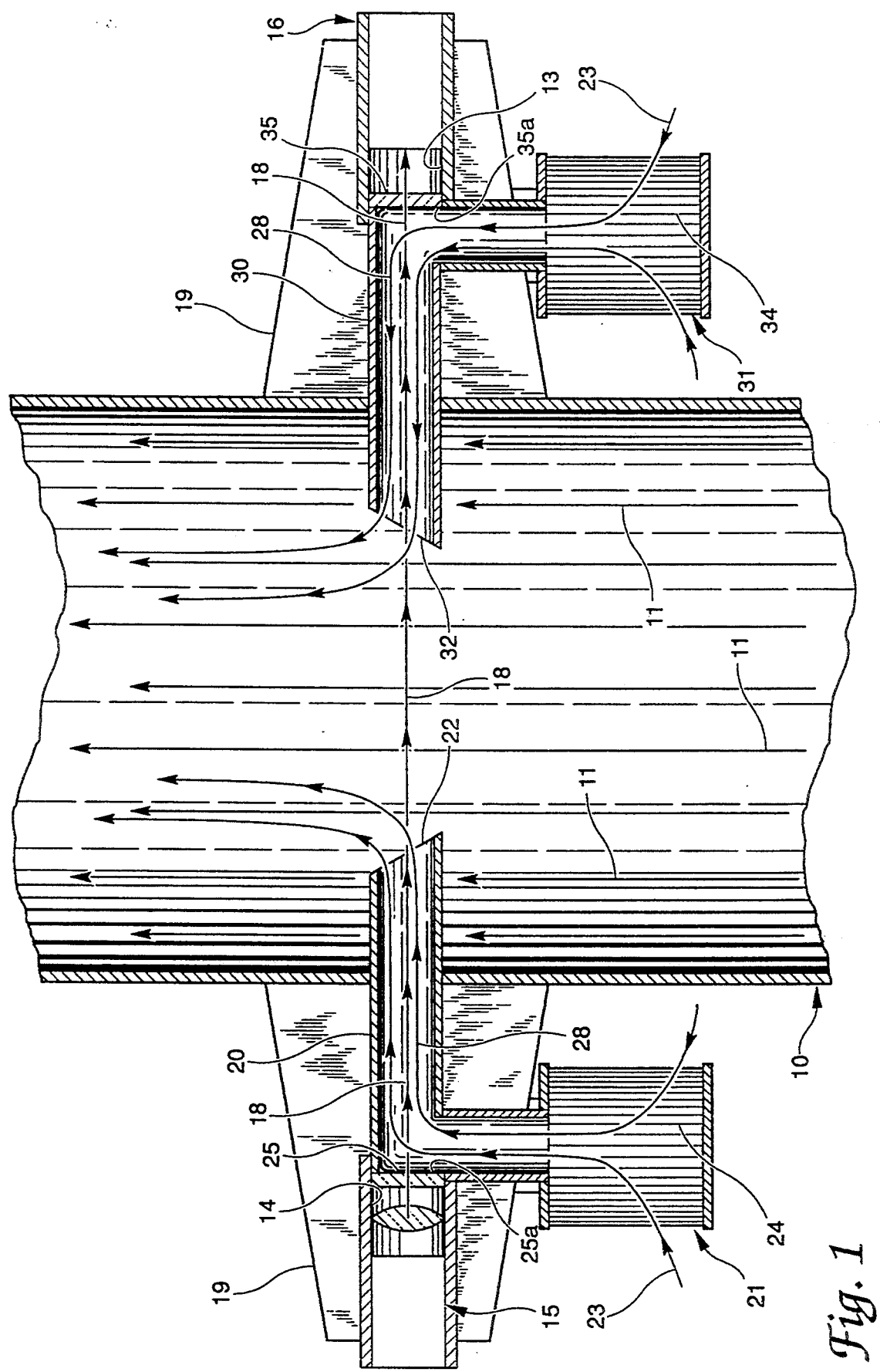
FIG. 1 is a sectioned side elevational view of a self-cleaning smoke-monitoring system according to the present invention.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawing, a portion of an exhaust pipe 10 conveys exhaust 11 in the direction of the arrows from an internal combustion engine (not shown) when the engine is running. A heat-resistant support 19 is attached to the illustrated segment of the exhaust pipe 10 and provides a platform upon which the various components of the smoke-monitoring system 12 are mounted. Smoke-monitoring system 12 of the present invention includes a sensor portion 16 and a light source 15 each mounted in its own sealed compartment 13 and 14, respectively. As discussed earlier, the sealed compartments protect the sensitive electrical and optical elements from potential contaminants. As optical path 18 extends between light source 15 and sensor 16, and traverses the exhaust pipe so that the opacity of exhaust stream 11 can be measured. A portion of optical path 18 coincides with L-shaped air ducts 20 and 30, respectively. Sealed compartment 14 and air duct 20 share a common wall portion in transparent window 25 which is positioned in optical path 18. Likewise, sealed compartment 13 and air duct 30 share a common wall in transparent window 35, which is also positioned in optical path 18.

L-shaped air duct 20 includes an inlet 21 that opens outside of exhaust pipe 10 and an outlet 22 that opens into the exhaust pipe. A filter 24 is positioned adjacent inlet 21 and serves to remove any particulate matter from ambient air 23 entering air duct 20. In a like manner, L-shaped air duct 30 includes an inlet 31 that opens outside of exhaust pipe 10 and an outlet 32 that opens into the exhaust pipe. Also, a filter 34 is positioned adjacent inlet 31 of L-shaped air duct 30. It is to be understood that ducts 20 and 30 could be merged to have a single inlet and a single filtering means instead of each having its own separate filter and inlet. In order to maintain the accuracy of the smoke-monitoring system, ambient air 23 is continually drawn into air ducts 20 and 30 so that particulate-free filtered air 28 continuously passes over the exposed faces 25a and 35a of windows 25 and 35, respectively. In this way, the exposed faces of windows 25 and 35 are maintained free of particulate matter and other contaminants that could interfere with the accuracy of the smoke-monitoring system.

By properly sizing and arranging outlets 22 and 32 as well as the cross-section of exhaust pipe 10 in the vicinity of outlets 22 and 32, a venturi effect can be created. In other words, the fluid pressure of exhaust stream 11 adjacent outlets 22 and 32 of the air ducts can be made to be lower than the air pressure adjacent inlets 21 and 31 so that ambient air 23 is continuously pulled into air ducts 20 and 30 when the engine is running. The venturi effect can be best explained in the context of the following well-known equation:

$$P_0 = P + \tfrac{1}{2}\rho V^2 = \text{Constant}$$

$P_0$ being the stagnation pressure of the fluid, P being the static fluid pressure, $\rho$ being the mass density of the fluid and V representing the velocity of the fluid. Assuming that the stagnation pressure $P_0$ and the fluid density $\rho$ are roughly constant for the given fluid, the static pressure P can be changed by alternating the velocity V of the fluid.

The velocity of the fluid (exhaust stream 11) can be easily controlled by exploiting the relationship between fluid velocity and the cross-sectional area of exhaust pipe 10. Because the mass flow rate of exhaust 11 is roughly constant along the length of exhaust pipe 10, exhaust stream 11 can be speeded up at a given location simply by reducing the cross-sectional area of the exhaust stream at that location. If the velocity of exhaust stream 11 is raised sufficiently, the static fluid pressure P can be made to drop below the ambient air pressure outside of the exhaust pipe. Thus, if outlets 22 and 32 of air ducts 20 and 30 are positioned in exhaust stream 11 at a point where the static fluid pressure P is below the ambient pressure outside the exhaust pipe, ambient air 23 will continually be drawn into the air ducts and flow into exhaust stream 11.

It is important to note that only a very small flow of filtered air 28 is required in order to prevent contamination of the exposed faces 25a and 35a of windows 25 and 35. Thus, in some instances, some means would need to be provided to limit the flow of air through air ducts 20 and 30. This could be accomplished by either reducing the surface areas of filters 24 and 34, by reducing the cross-section of the air ducts between the inlet and the windows 25 and 35, or by controlling the inlet area to the filters. In any event, the flow of filtered air 28 through air ducts 20 and 30 should be kept near a minimum so that the filtered air 28 will not affect the cross-section of exhaust pipe 10 which is traversed by optical path 18, thereby ensuring the accuracy of the smoke-monitoring system. Proper care should also be used in installing the system so that contaminants will not fall from the exhaust pipe 10 down into air ducts 20 and 30 when the engine is not operating.

Inlets 21 and 31 are preferably positioned in a dead air space. When the engine being evaluated is actually mounted in a vehicle, inlets 21 and 31 can be positioned on the vehicle in the direction of travel such that ram pressure is created at the inlets 21 and 31 to further increase the flow of air through air ducts 20 and 30 if necessary. In general, however, it may be desirable to protect inlets 21 and 31 from moving air currents in order to prevent instances of flow reversal in air ducts 20 and 30 which would bring contaminated air from within exhaust pipe 10 into contact with the exposed faces 25a and 35a of windows 25 and 35.

While the invention has been illustrated and described in detail in the drawings and foregoing description, the same is to be considered as illustrative and not restrictive in character. For instance, while the preferred embodiment includes a filter means to remove particulate matter from the ambient air entering the air ducts, the smoke-monitoring system of the present invention could operate without a filter provided the inlet to the air ducts was positioned in an area that pulled in relatively particulate-free air. It is to be understood that only the preferred embodiment has been shown and described and that all changes and modifications that come within the spirit of the invention are desired to be protected.

What is claimed is:

1. A self-cleaning smoke-monitoring system for use in measuring opacity of exhaust from an internal combustion engine, comprising:
   an exhaust pipe attached to the engine for conveying exhaust from the engine;
   a light source and sensor combination defining an optical path therebetween that traverses said exhaust pipe;
   a first air duct having a first outlet that opens into said exhaust pipe and a portion that coincides with said optical path;
   a first window positioned in said optical path and attached to said first air duct, said light source being positioned outside said first air duct and adjacent said first window;
   a second air duct having a second outlet that opens into said exhaust pipe and a portion that coincides with said optical path;
   a second window positioned in said optical path and attached to said second air duct, said sensor being positioned outside said second air duct and adjacent said second window;
   inlet means attached to said air ducts for supplying ambient air to said air ducts;
   filter means attached to said air ducts for removing particulate matter from ambient air entering said air ducts through said inlet means; and
   a portion of said first air duct between said first window and said first outlet, and a portion of said second air duct between said second window and said second outlet, extending into said exhaust pipe and restricting the cross-sectional area of said exhaust pipe to create a venturi effect in the vicinity of said first and second outlets when the engine is running such that the fluid pressure of the exhaust from the engine adjacent said outlets is lower than the air pressure at said inlet means, said venturi effect causing air to be pulled through said first and second air ducts to thereby prevent said exhaust from contaminating said first and second windows.

2. The self-cleaning smoke-monitoring system of claim 1 further comprising means for limiting air flow through said air ducts so that said air flow has a negligible influence on measurements made by said light source and sensor combination.

3. The self-cleaning smoke-monitoring system of claim 1 wherein said inlet means is a first inlet attached to said first air duct that opens outside of said exhaust pipe and a second inlet attached to said second air duct and opening outside of said exhaust pipe.

4. The self-cleaning smoke-monitoring system of claim 3 wherein said filter means is a first filter positioned within said first air duct between said first inlet and said first window and a second filter positioned within said second air duct between said second inlet and said second window.

5. The self-cleaning smoke-monitoring system of claim 4 wherein said first inlet and said second inlet are positioned within a dead air space.

6. A self-cleaning smoke-monitoring system for use in measuring opacity of exhaust from an internal combustion engine, comprising:

an exhaust pipe attached to the engine for conveying exhaust from the engine;

a light source and sensor combination defining an optical path therebetween that traverses said exhaust pipe;

a first air duct having a first outlet that opens into said exhaust pipe and a portion that coincides with said optical path;

a first window positioned in said optical path and attached to said first air duct, said light source being positioned outside said first air duct and adjacent said first window;

a second air duct having a second outlet that opens into said exhaust pipe and a portion that coincides with said optical path;

a second window positioned in said optical path and attached to said second air duct, said sensor being positioned outside said second air duct and adjacent said second window;

inlet means attached to said air ducts and opening into a relatively dead air space for supplying ambient air to said air ducts; and a portion of said first air duct between said first window and said first outlet, and a portion of said second air duct between said second window and said second outlet, extending into said exhaust pipe and restricting the cross-sectional area of said exhaust pipe to create a venturi effect in the vicinity of said first and second outlets when the engine is running such that the fluid pressure of the exhaust from the engine adjacent said outlets is lower than the air pressure at said inlet means, said venturi effect causing air to be pulled through said first and second air ducts to thereby prevent said exhaust from contaminating said first and second windows.

7. The self-cleaning smoke-monitoring system of claim 6 further comprising filter means attached to said air ducts for removing particulate matter from ambient air entering said air ducts through said inlet means.

8. The self-cleaning smoke-monitoring system of claim 6 further comprising means for limiting air flow through said air ducts so that said air flow has a negligible influence on measurements on said light source and sensor combination.

9. The self-cleaning smoke-monitoring system of claim 6 wherein said inlet means is a first inlet attached to said first air duct that opens outside of said exhaust pipe and a second inlet attached to said second air duct and opening outside of said exhaust pipe.

10. The self-cleaning smoke-monitoring system of claim 9 wherein said filter means is a first filter positioned within said first air duct between said first inlet in said first window and a second filter positioned within said second air duct between said second inlet and said second window.

* * * * *

UNITED STATES PATENT AND TRADEMARK OFFICE
CERTIFICATE OF CORRECTION

PATENT NO. : 5,424,842
DATED : June 13, 1995
INVENTOR(S) : Richard N. Poorman

It is certified that error appears in the above-identified patent and that said Letters Patent is hereby corrected as shown below:

In Column 2, at line 21, please replace "that" with --than--.

Signed and Sealed this

Twelfth Day of September, 1995

Attest:

BRUCE LEHMAN

Attesting Officer    Commissioner of Patents and Trademarks